(12) United States Patent
Wardlaw

(10) Patent No.: US 6,402,784 B1
(45) Date of Patent: Jun. 11, 2002

(54) INTERVERTEBRAL DISC NUCLEUS PROSTHESIS

(75) Inventor: Douglas Wardlaw, Stonehaven (GB)

(73) Assignee: Aberdeen Orthopaedic Developments Limited, Stonehaven (GB)

(*) Notice: Subject to any disclaimer, the term of this patent is extended or adjusted under 35 U.S.C. 154(b) by 0 days.

(21) Appl. No.: 09/462,442

(22) PCT Filed: Jul. 10, 1998

(86) PCT No.: PCT/GB98/02017
§ 371 (c)(1),
(2), (4) Date: Jan. 7, 2000

(87) PCT Pub. No.: WO99/02108
PCT Pub. Date: Jan. 21, 1999

(30) Foreign Application Priority Data

Jul. 10, 1997 (GB) .............................................. 9714580

(51) Int. Cl.⁷ .................................................. A61F 2/44
(52) U.S. Cl. .................................................... 623/17.11
(58) Field of Search ........................... 623/17.12, 17.16, 623/8, 17.11

(56) References Cited

U.S. PATENT DOCUMENTS

| 3,867,728 A | 2/1975 | Stubstad et al. |
| 3,875,595 A | 4/1975 | Froning |
| 3,975,350 A | 8/1976 | Hudgin et al. |
| 4,944,749 A * | 7/1990 | Becker .......................... 623/8 |
| 4,969,888 A | 11/1990 | Scholten et al. |
| 5,171,280 A * | 12/1992 | Baumgartner ............. 623/17.12 |
| 5,192,326 A * | 3/1993 | Bao et al. ................ 623/17.12 |
| 5,456,716 A * | 10/1995 | Iversen et al. ................. 623/8 |
| 5,645,597 A | 7/1997 | Krapiva |
| 5,976,186 A * | 11/1999 | Bao et al. ................ 623/17.12 |
| 6,022,376 A * | 2/2000 | Assell et al. ............. 623/17.12 |
| 6,110,210 A * | 8/2000 | Norton et al. ........... 623/17.16 |
| 6,132,465 A * | 10/2000 | Ray et al. ................ 623/17.16 |
| 6,187,048 B1 * | 2/2001 | Milner et al. ............ 623/17.12 |

FOREIGN PATENT DOCUMENTS

| DE | 39 22 203 C1 | 10/1990 |
| EP | 0 277 282 A1 | 10/1988 |
| FR | 2 723 841 A1 | 1/1996 |
| WO | WO 92/10982 | 7/1992 |
| WO | WO 95/31948 | 11/1995 |
| WO | WO 96/11642 | 4/1996 |

* cited by examiner

Primary Examiner—David H. Willse
Assistant Examiner—Suzette J. Jackson
(74) Attorney, Agent, or Firm—Lawrence E. Laubscher, Jr.

(57) ABSTRACT

The present invention provides a prosthetic cover (12) shaped to form a replacement nucleus pulposis (56) for an intervertebral disc (50), said cover comprising a permeable layer of an immunologically neutral material terminating in a valve structure (16) to allow the introduction of a hydrogel material (14); characterized in that a transudative material is disposed on the intended inner face of the cover to allow a through flow of low molecular weight materials only.

16 Claims, 8 Drawing Sheets

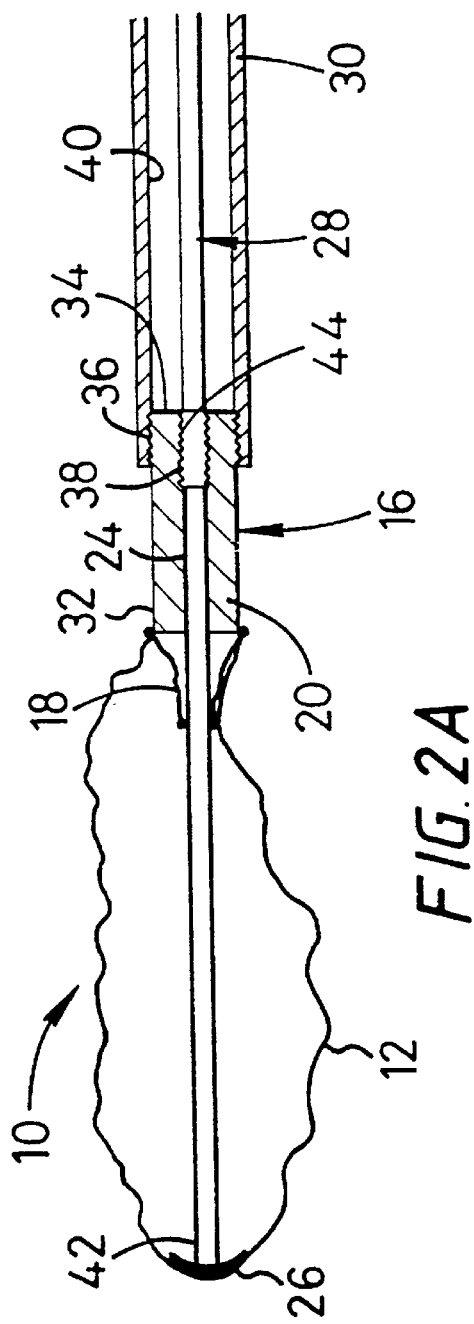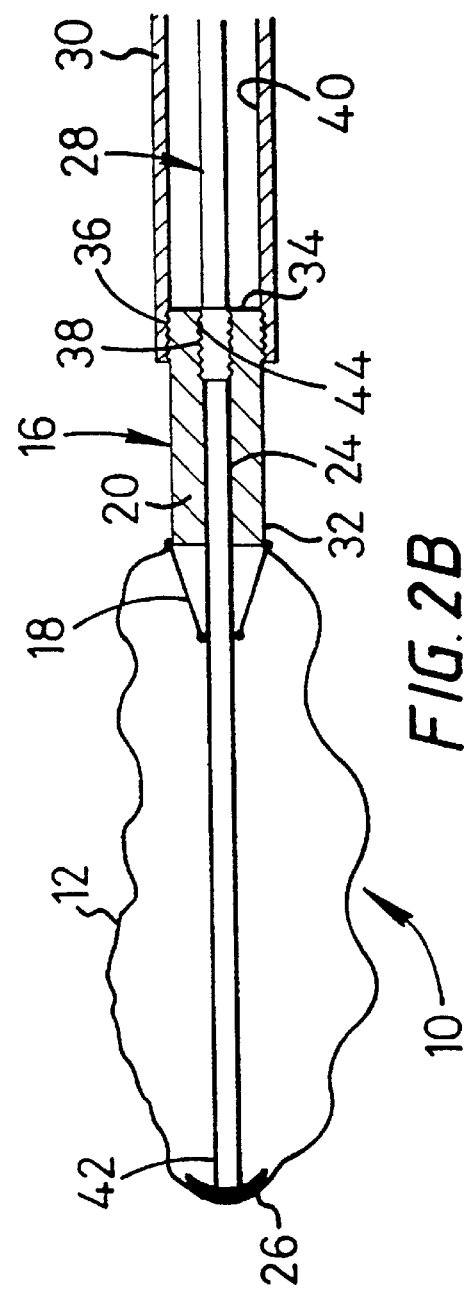

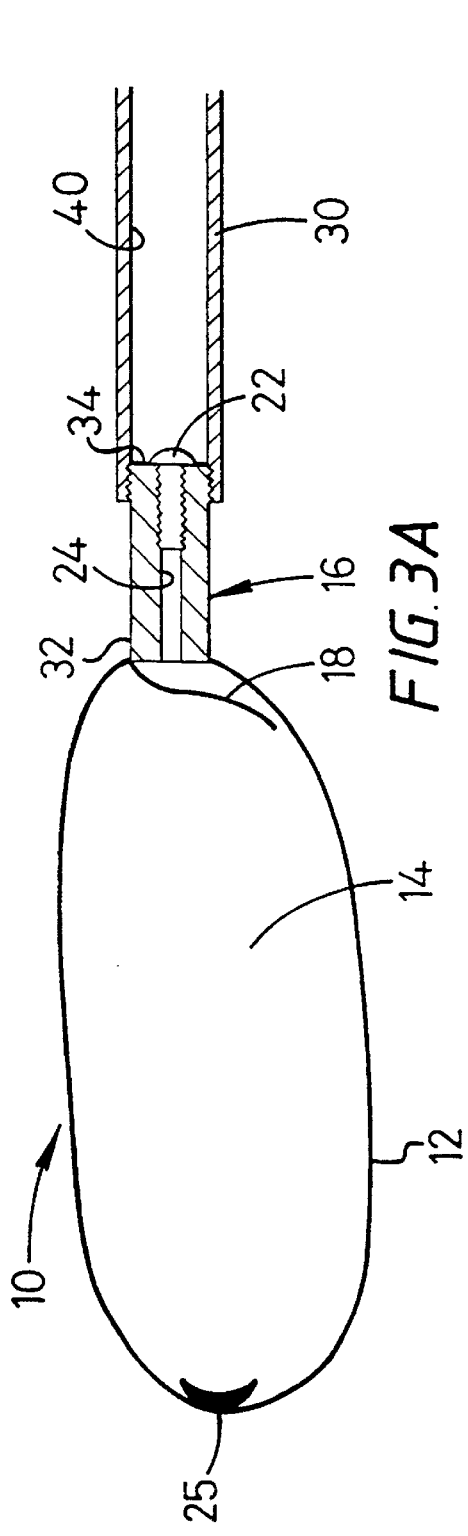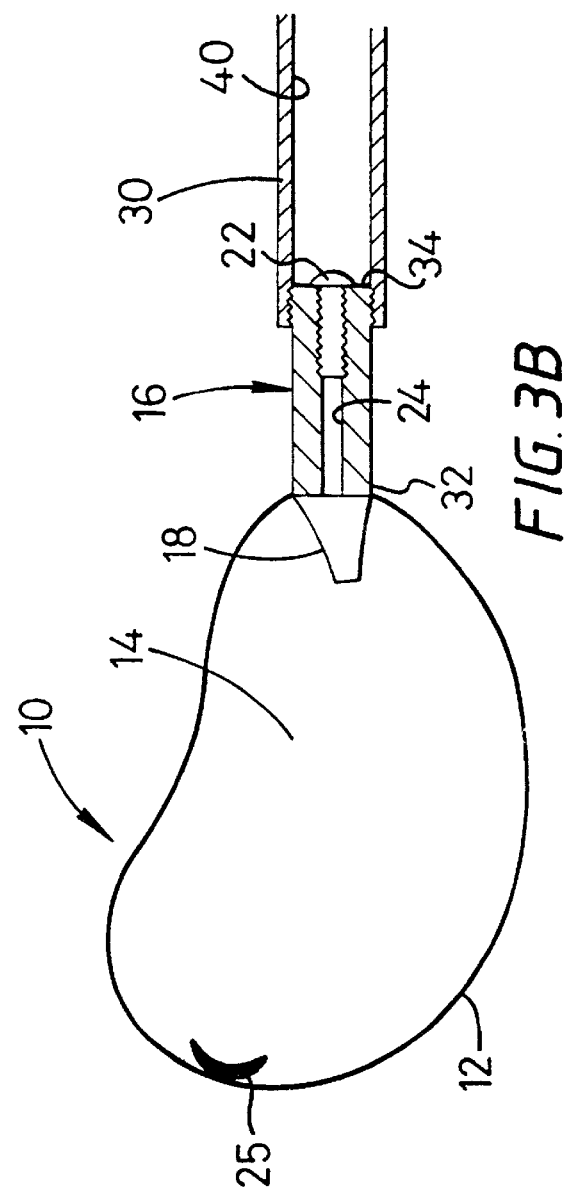

FIG. 4
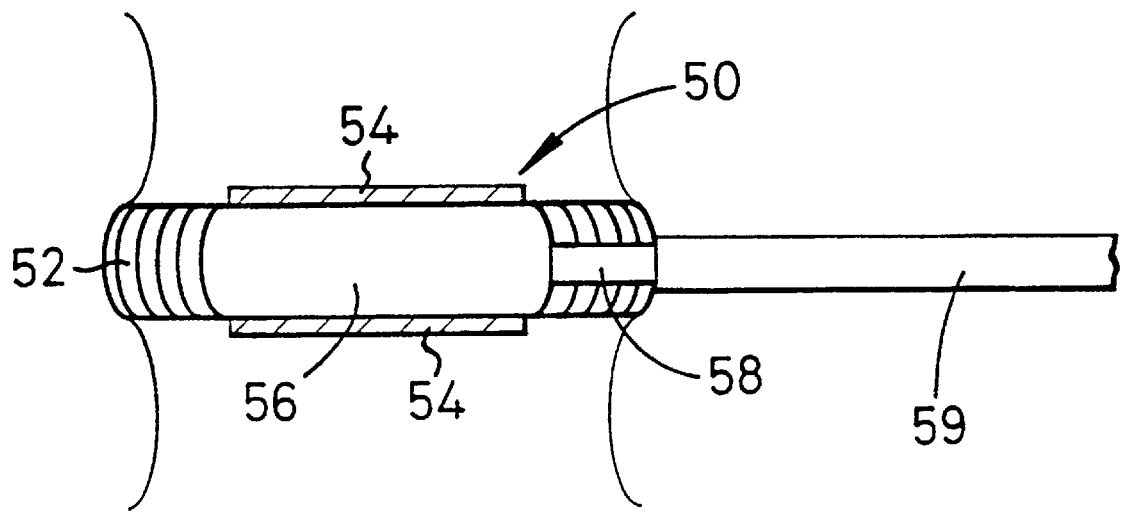
FIG. 4A
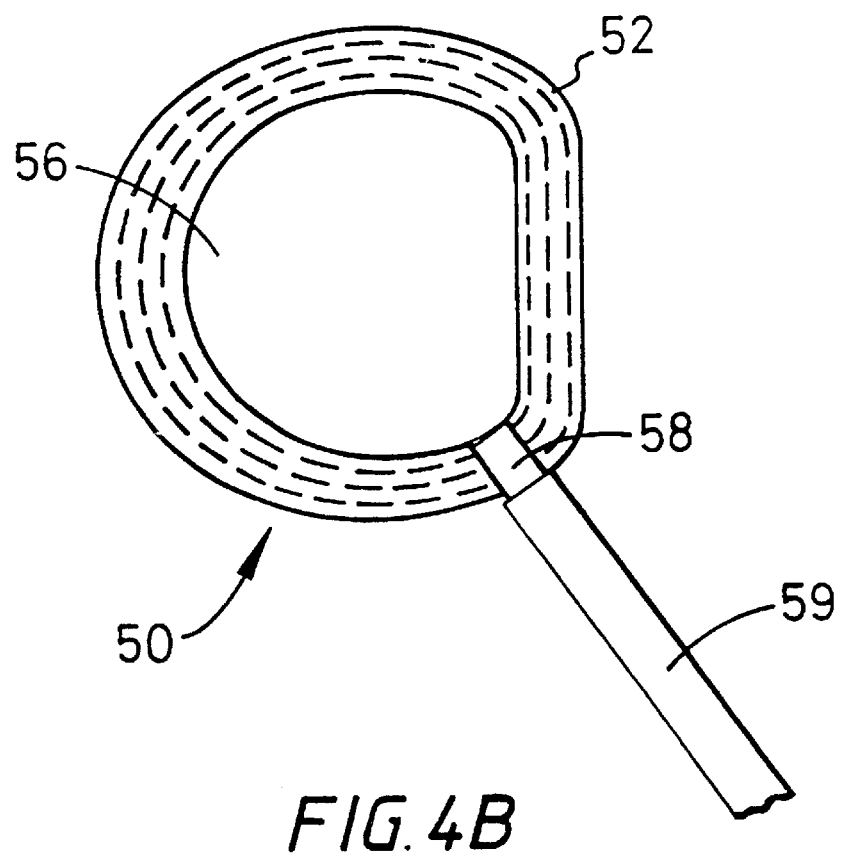
FIG. 4B

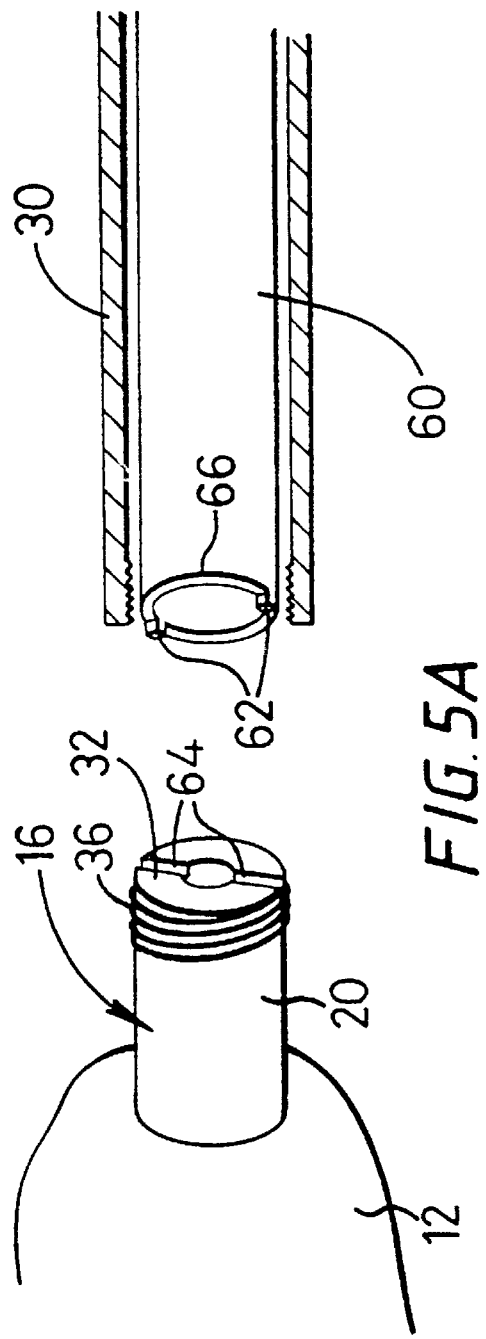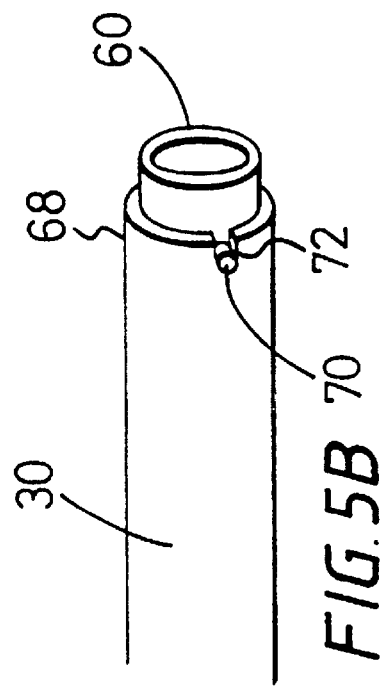

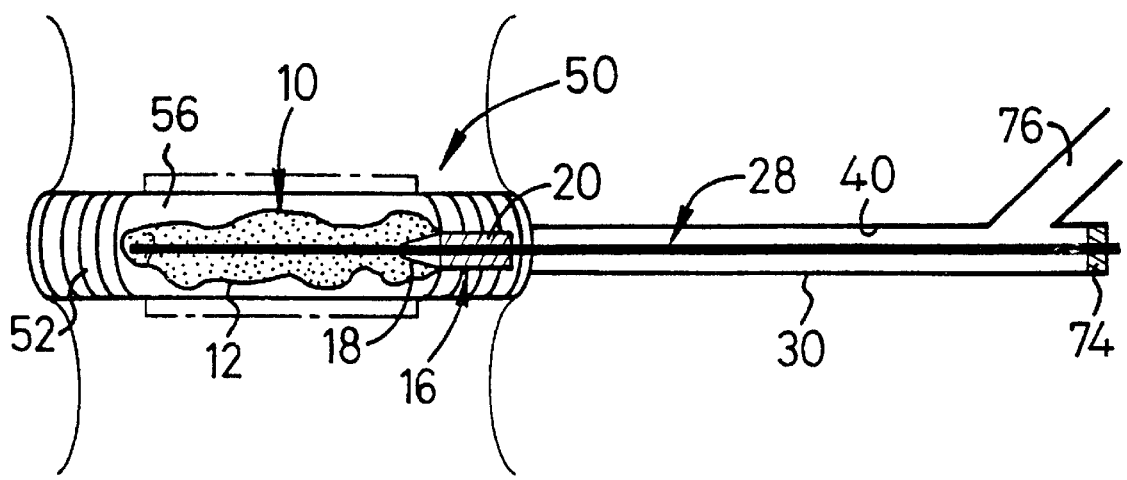
FIG. 6
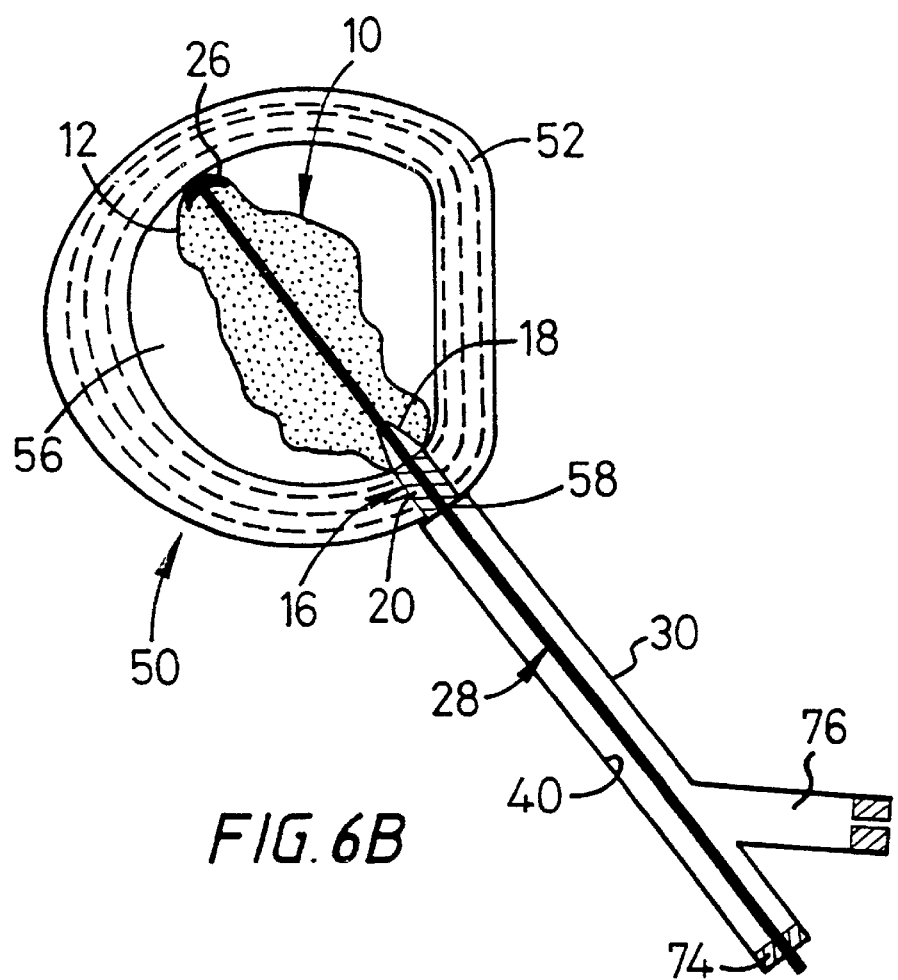
FIG. 6A
FIG. 6B

FIG. 7
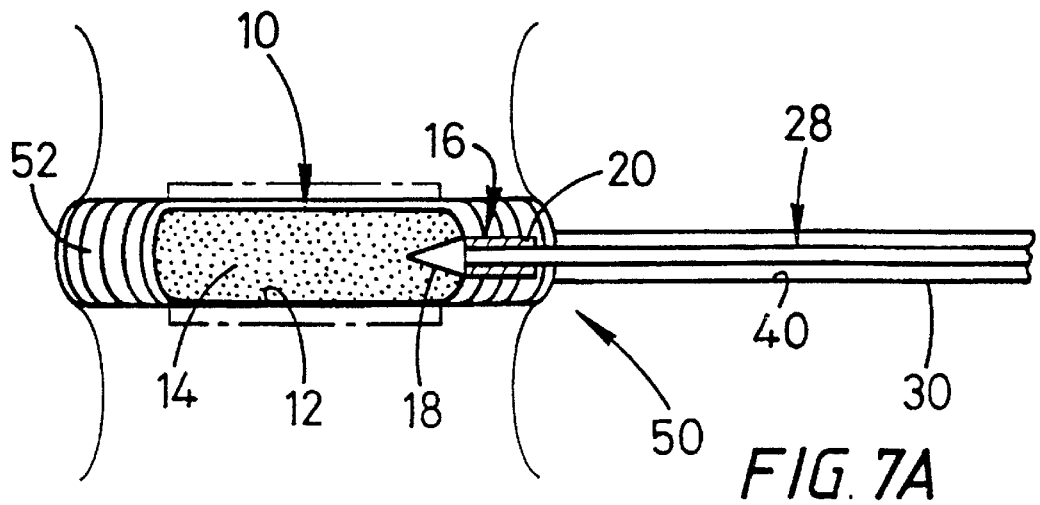
FIG. 7A
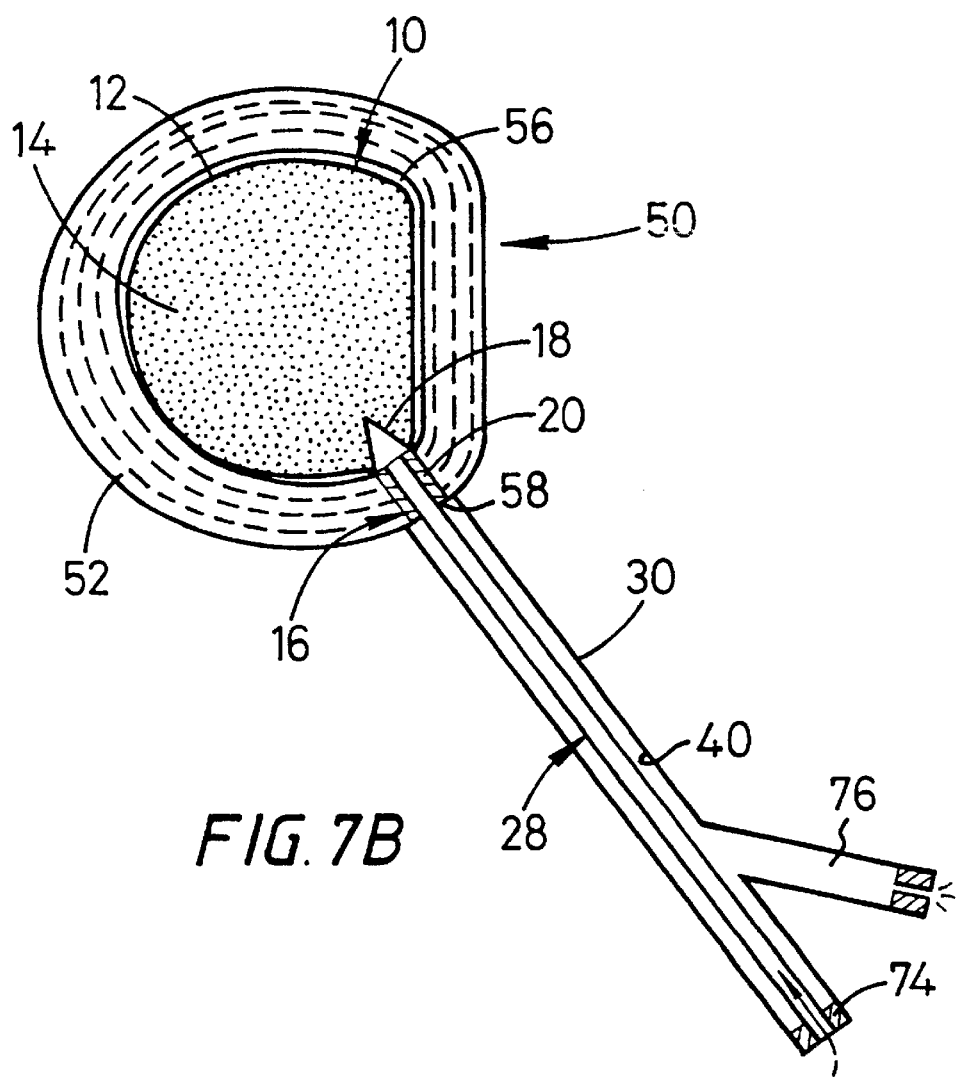
FIG. 7B

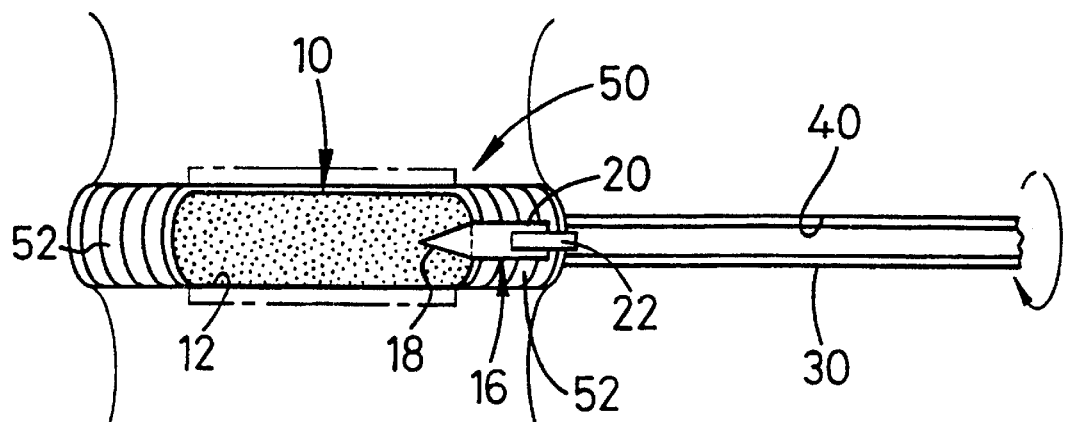
FIG. 8A
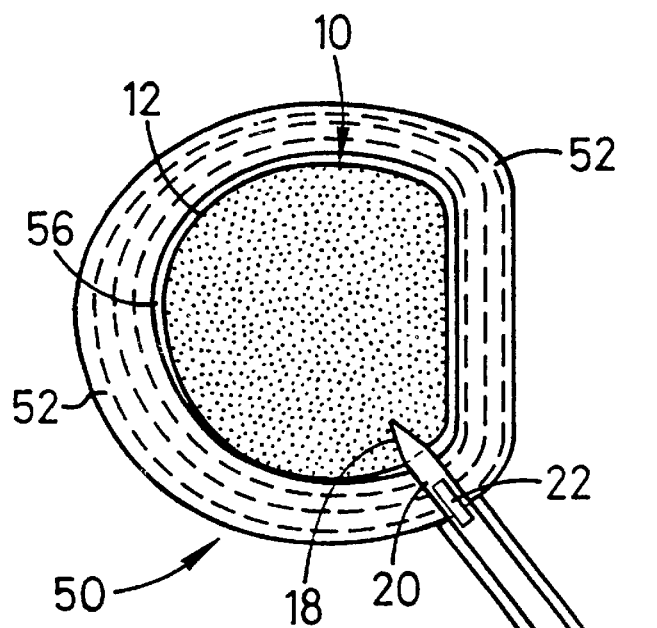
FIG. 8B
FIG. 8
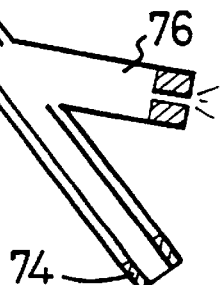

INTERVERTEBRAL DISC NUCLEUS PROSTHESIS

The present invention relates to a prosthetic intervertebral disc nucleus and to an insertion device for use therewith. Such devices are useful to replace damaged disc nuclei, whether in the lumbar or other region of the spine.

The normal intervertebral disc is a highly specialized joint between the intervertebral bodies from the second cervical vertebra to the first sacral vertebra in the human being. A disc is made up of a strong outer ring called the annulus which is strongly attached to the intervertebral bodies above and below through collagen fibers, and a central nucleus. The nucleus comprises a mesh of collagen fibers to which is attached proteoglycan molecules which are hygroscopic. It can therefore be said to consist of a central portion and an intermediate zone. The central portion comprises 90% proteoglycan and 10% collagen, and the intermediate zone rather less proteoglycan and proportionately more collagen. The annulus comprises 90% collagen with about 10% proteoglycan, which proteoglycan acts to allow a sliding motion between adjacent layers during normal daily use.

Like all other joints in the body, intervertebral discs, particularly lumbar intervertebral discs, are subject to various types of injury, degeneration and disease. Painful disc syndromes can develop due to the destruction of the intervertebral disc structure.

It is often the case that back pain emanating from an intervertebral disc arises from a damaged annulus because the annulus itself is the only part of the disc structure which is innervated. In theory then, the insertion of a prosthesis which has itself a finite structure with inherent strength but at the same time is held in position by the annulus would permit the annulus itself to heal with the commensurate relief of pain.

Various disc prostheses are known in the art for example from U.S. Pat. No. 3,875,595 and WO 95/31948. There are various problems associated with these. In U.S. Pat. No. 3,875,595, there is provided a collapsible plastic bladder prosthesis of the same exterior form as the nucleus pulposis of an intervertebral disc. This is provided with a stem through which liquid/plastic is introduced to inflate the prosthesis to a natural form. The difficulty with this arrangement is that since the exterior of the bladder-like prosthesis is impermeable, the prosthesis is not anchored and hence must be provided with external studs to secure the same in the position relative to adjacent vertebrae. Such an arrangement tends to adversely impact upon the adjacent vertebrae and/or the plastic sheath of the prosthesis, and bearing in mind the trauma associated with insertion and subsequent repair where necessary, such arrangements have not been found to be satisfactory.

In part, these problems have also been addressed in WO 95/31948. This provides an expandable fabric insert for stabilizing spinal motion which allows through growth of living cells, unlike other prior art prostheses. This can be inserted by open operation. This arrangement is designed to be filled with bone graft or bone substitute material with a view to bringing about a solid bone fusion or a fibrous fusion. For anchoring purposes it is of course necessary for the living cells to grow through the woven material of the prosthetic cover and this in fact can occur.

Alternatives have been suggested, for example in U.S. Pat. No. 5,674,295. This describes a nuclear prosthesis which has an outer restraining jacket surrounding a hydrogel, and optionally other materials. In the dehydrated state, the hydrogel has a volume smaller than the constraining jacket but when hydrated is constrained within the jacket so it can conform to a certain extent to external loads placed upon it. The prosthesis is always of a smaller volume than the nuclear space in which it is placed, but on hydration increases the disc height, tensioning the fibers of the annulus.

Another attempt at this has been in WO 92/10982 in that a prosthesis of the type of this invention is revealed with a supported membrane being approximately above 15,000 daltons, or 25A. While this approach may be viable, better results, especially in terms of immunological disturbances may be achieved if significantly lower porosity is utilized without rendering the cover completely impermeable.

What is required therefore is a prosthesis which can be introduced with the minimum of trauma via the lateral percutaneous route, which stays correctly anchored in position, which allows some exchange of fluid and low molecular weight materials, but without immunological problems, and/or acts over the majority of the articulating surfaces of the adjacent vertebrae.

SUMMARY OF THE INVENTION

The present invention is directed towards an intervertebral disc nucleus prosthesis generally comprising a transudative or ion transport material extended over the inner face of a prosthetic woven or porous fabric chosen for its strength and immunological neutrality. With this design, tissue can grow over and incorporate the outer fabric, while water and very low molecular weight materials can pass the prosthetic fabric and the transudative membrane, thus eliminating, or at least substantially alleviating, any immunological problems. This allows the anchoring of the replacement nucleus pulposis within a disc space while preventing the ingrowth of bony trabeculae, thereby providing a more satisfactory long term solution.

An alternative embodiment generally comprises a three layer cover, wherein the outer and inner layer are formed of a strong material in a sandwich construction with a middle layer of a transudative material of a small pore size. Very high pressures are present in use within the normal disc nucleus. To counteract this it is often necessary to introduce a hydrogel or other suitable substance into the cover in a liquid or powdered state. Thus, the hydrogel would have a tendency to escape through the cover were it not so constructed as to combine strength with an ability to retain the hydrogel which might otherwise leak out through the pores in the cover. The alternative jacket construction addresses this concern.

According to a first aspect of the invention therefore there is provided a prosthetic cover shaped to form a replacement nucleus pulposis of an intervertebral disc. The cover comprises a permeable layer of an immunologically neutral material and a transudative material adapted to allow the through flow of selected low molecular weight materials only. The cover terminates in a valve structure configured to allow the normally irreversible introduction of a hydrogel material. In one preferred embodiment, the valve structure includes a one way valve. In another preferred embodiment, the prosthetic cover comprises a three layered cover, preferably forming a sandwich construction having a middle layer of a transudative material.

The term "normally irreversible" it will be understood refers to the situation in use. Clinical situations can arise wherein it is desirable to change the volume of hydrogel in the cover post-operatively. This may be achieved by causing the hydrogel to flow out of the cover by re-opening the valve structure in a fashion analogous to the filling operation, liquidizing the hydrogel and then applying a vacuum.

Regardless of the number of layers comprising the cover, the cover further includes in one preferred embodiment, a strengthening member opposite the valve structure. The strengthening member is preferably integrally formed to the material comprising the cover and is configured to selectively receive an end of an introducer rod during implantation of the prosthesis. In this regard, the strengthening member allows a user to apply a pushing force on the cover without causing any tears.

As is clear from the foregoing, the low molecular weight materials may include water and other low molecular weight materials present in the environment of use. The immunologically neutral material may be woven and is particularly satisfactory if selected from "Dacron"® and "Gortex"®, but other similar materials with the same MW cut off characteristics are also suitable, for example those described in U.S. Pat. No. 5,674,295.

The transudative material membrane is preferably adapted to have a molecular cut off below 100 Angstroms, or 12,000 daltons, more preferably below 9,000 daltons. In particularly preferred embodiments, the transudative membrane material has a molecular cut off of up to MW500, but may be as low as MW200 or even MW50. In a particularly favoured composition the transudative membrane material may comprise "Opsite"®.

The valve structure is preferably formed of an imaging transparent material, for example titanium, carbon fibre or a durable biocompatible plastics material such as polypropylene. In one preferred embodiment, the valve structure includes a one way valve arrangement which may be a flap valve partially attached to an inside of the cover, making it more certain that the valve structure will be in a closed state when an internal pressure of the cover exceeds an exterior or injection pressure of the hydrogel material. Alternatively, the one way valve arrangement may be a conical nose with a narrower internal opening, again directing the valve structure to a closed state under similar circumstances. The conical configuration facilities insertion of an introducer rod, as described below.

In one alternative embodiment, the valve structure further includes an extension body attached to the one way valve arrangement. The extension body may be external to the cover, or partially or totally inside it. With one preferred option, the extension body is external or partially external relative to the cover to allow attachment of an external introducer tube that controls the whole process of implantation, as described below. The extension body preferably has a central longitudinal bore which is provided over a part thereof with an internal screw thread.

The hydrogel is preferably a polyvinyl alcohol material, such as "HYPAN"®, developed into a fluid or liquid form which will easily pass through the valve structure and subsequently harden. Ideally, the swelling pressure of the resultant hydrogel is in a range similar to, or as close as possible to, a normal lumbar intervertebral disc.

The prosthesis of the present invention is preferably sized such that an internal surface area of a nuclear cavity is virtually the same as the prosthetic cover. This will ensure that load distribution within the resulting prosthesis is similar to that of a normal intervertebral disc. The technology of hydrogels at the present time means that the swelling pressure of hydrogel can only approximate to one quarter or one third of a normal disc. So to retain their ability to maintain disc height, it is preferable to form the hydrogel as a solid material, or that the hydrogel harden or "cure" following injection into the cover. In one alternative embodiment, a fine wire of a radiolucent material is incorporated within the prosthesis to demonstrate the position of a prosthesis in vivo.

In use, one preferred method of insertion of a prosthesis in accordance with the present invention is as follows:

A skin incision is made adjacent a damaged intervertebral disc, including an annulus and a nucleus, which has previously been extensively imaged by a Computer Tomography or Magnetic Resonance Imaging. If necessary, confirmation that it is the disc which is painful may be reached by effecting provocative stress discography. This allows percutaneous disc surgery to be carried out by a lateral approach whereby a cannula or trochar is used to insert instruments laterally between adjacent vertebrae in the spine through the paraspinal musculature so entering the disc at the postlateral corner in the "safe" triangle; inferior to the exiting nerve root. The incision provides for access to the nucleus portion of the intervertebral disc.

Chymopapain may be injected into the nucleus to digest the proteoglycan structure thereof. Mechanical action as by a brush with polypropylene bristles may be used to aid the breakdown of any remaining collagen structure to enhance the effect of chymopapain which may then be removed by suction. Subsequently an intervertebral disc nucleus prosthesis in accordance with the present invention is introduced through the disc annulus. The disc annulus comprises an outer ring of strong collagenous fibrous tissue. As previously described, the prosthesis preferably includes a cover and a valve structure. The valve structure, in one preferred embodiment, includes the one-way valve arrangement (or conical nose) and an extension body that may be knurled or fluted as appropriate. A strengthening member may be incorporated into the cover immediately opposite the valve structure for receiving an introducer rod. This allows the relatively atraumatic insertion of the prosthesis cover through the annulus into the space created by the removed nucleus.

Prior to insertion, the prosthesis is preferably attached to an external introducer tube. In one preferred embodiment, a distal end of the external introducer tube is internally threaded to selectively engage external threads of the extension body. Thus, the external introducer can be selectively secured to the valve structure. Additionally, a tubular screw driver may be provided. The tubular screw driver is sized to be coaxially received within the external introducer tube. Further, a distal end of the tubular screw driver is preferably configured to selectively mate with both the extension body of the valve structure, as well as with the distal end of the external introducer tube. With this preferred design, the tubular screw driver controls actuation of the valve structure and attachment between the valve structure and the external introducer tube. Finally, the introducer rod is coaxially positioned within the external introducer tube.

In one preferred embodiment, the introducer rod is preferably externally threaded to threadably engage an internal thread on the longitudinal bore of the valve structure. The introducer rod serves as a temporary stiffening device, allowing a surgeon to apply a pushing force on the cover. Thus, with proper positioning of the introducer rod, which may be seated in the strengthening member of the cover, the surgeon can extend the prosthesis cover into the cavity between adjacent vertebrae.

Once the prosthesis is positioned within the disc space, the introducer rod is withdrawn. Hydrogel material is then introduced into the prosthesis cover via a syringe connected to the external introducer tube. In one preferred embodiment, a distal end of the syringe is directed through the external introducer tube and secured to the valve structure. With this approach, the syringe has an internal seal, to ensure that the hydrogel material passes through the valve structure into the cover, and a locking mechanism to ensure a tight seal with the valve structure. The syringe of this embodiment further includes a tubular piston rod and a piston that is selectively secured to a screw configured to immediately close the valve structure after injection of the hydrogel. In one embodiment, once a desired volume of hydrogel has been injected into the cover of the prosthesis, and the piston is at the bottom of the syringe, a screw driver may be passed down a center of the piston to insert and tighten the screw to the valve structure. Alternatively, the screw and the screw driver may be incorporated together into the piston, and the piston rod simply turned to secure the screw to the valve structure.

Alternatively, the external introducer tube may be a cannula including two proximal ports to facilitate injection of the hydrogel material. With this configuration, a syringe is secured to one of the two proximal ports. Hydrogel material is forced from the syringe into the external introducer tube. The external introducer tube, in turn, directs the hydrogel material to the valve structure and then into the prosthetic cover. With the prosthesis filled adequately with hydrogel material to a desired internal pressure, a screw is then passed through the external introducer tube and secured to the valve structure so as to retain the contents of the prosthesis. In the event that the volume of hydrogel material needs to be subsequently altered, this can be performed in a substantially non-traumatic way by merely removing the screw and replacing the contents of the prosthesis cover as necessary.

Another aspect of the present invention relates to a valve structure adapted for use in a prosthetic device. The valve structure preferably comprises a valve body with a longitudinal bore therein, obturating means associated with said bore and attachment means. The valve body is configured to be fluidly secured to a cover of the prosthetic device. For example, an exterior portion of the valve body may be attached to the cover such that the longitudinal bore is in fluid communication with an interior of the cover. The obturating means is configured to selectively allow passage of filler material, such as hydrogel through the longitudinal bore. Finally, the attachment means is configured to selectively engage a material injection tool. The material injection tool is preferably an external introducer tube, cannula or similar apparatus designed to selectively engage a distal end of the material injection tube. In one preferred embodiment, the material injection tube is adapted to accommodate an introducer rod while also allowing injection of material to the valve structure.

The longitudinal bore of the valve body is preferably internally screw threaded for engagement with either the obturating means or an introducer rod, a syringe, material injection tube or screw as appropriate. The valve body may be generally symmetrical and the bore may extend axially within the valve body. Preferably the valve body is formed of an imaging transparent material, for example titanium, carbon fibre or a durable, biocompatible, plastics material such as polypropylene.

One aspect of the present invention will now be described in detail by way of illustration only with reference to the accompanying drawings.

FIG. 2A is an enlarged side sectional view of the prosthesis of FIG. 1A in a deflated state, including an introducer rod and external introducer tube;

FIG. 2B is an enlarged, top sectional view of the arrangement of FIG. 2A;

FIG. 3A is an enlarged, side sectional view of the prosthesis of FIG. 1A in an inflated state;

FIG. 3B is an enlarged, top sectional view of the arrangement of FIG. 3A;

FIG. 4 shows in FIG. 4A a vertical section through an intervertebral disc in the process of removal of a damaged nucleus pulposis;

FIG. 4B shows the same view in transverse cross-section;

FIG. 5A is an enlarged view of a valve structure and tubular screw driver in accordance with the present invention;

FIG. 5B is an enlarged view of the tubular screw driver and external introducer tube;

FIG. 6, shows in FIG. 6A a cross-section a prosthetic cover in accordance with the present invention being introduced between adjacent vertebrae, whereas FIG. 6B shows the same view of the cover in accordance with the present invention being introduced in transverse cross-section;

FIG. 7 shows in FIG. 7A the insertion of a hydrogel into the prosthesis in accordance with the present invention in vertical cross-section, whereas FIG. 7B shows the same view in transverse section; and FIG. 8 shows in FIG. 8A a vertical cross-section of the completed prosthesis, while FIG. 8B shows the same view as FIG. 8A in transverse cross-section;

Figure 1A:
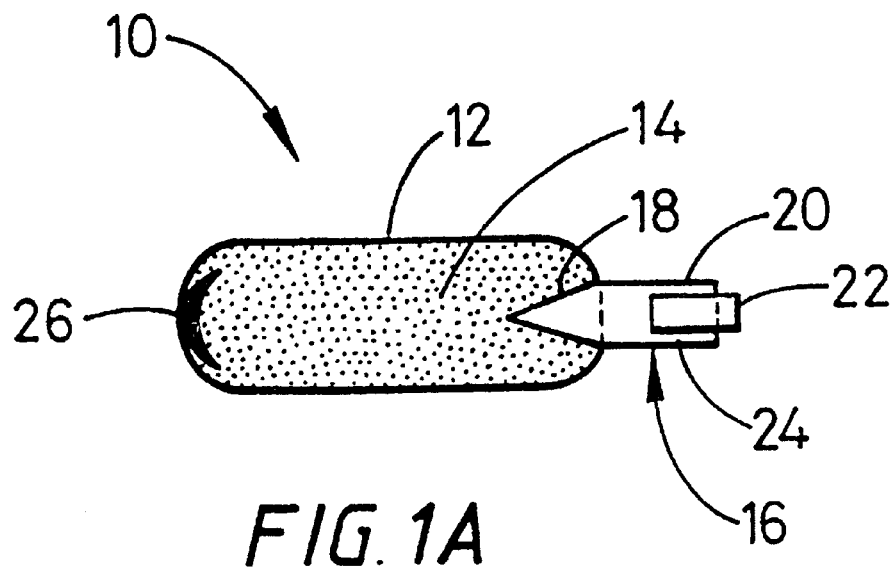
FIG. 1A is a side sectional view of an intervertebral disc nucleus prosthesis in accordance with the present invention.
Figure 1B:
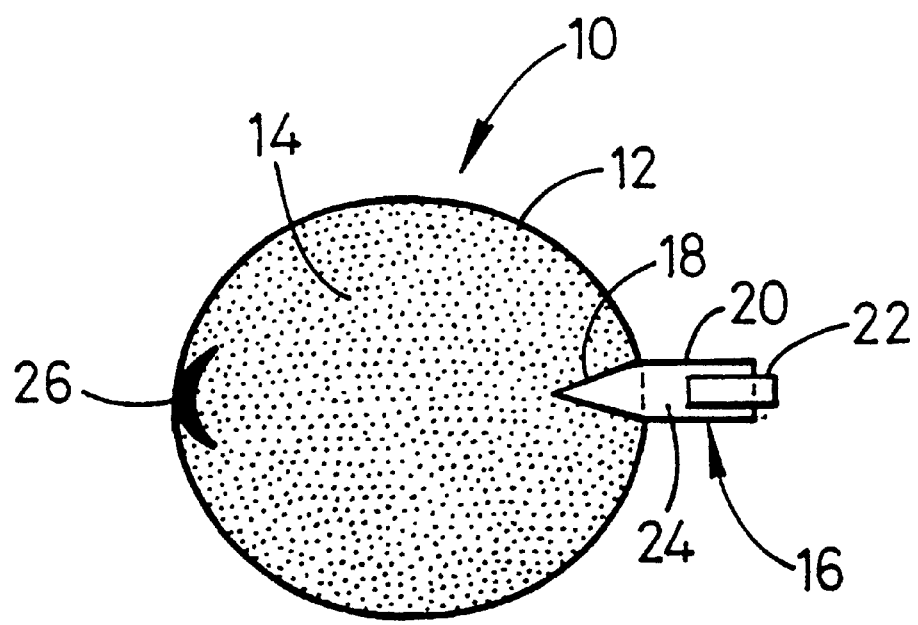
FIG. 1B is a top sectional view of the prosthesis of FIG. 1A.

One embodiment of an intervertebral disc nucleus prosthesis 10 is shown in FIGS. 1A and 1B. The prosthesis 10 includes a cover 12, a filler material 14 and a valve structure 16. The cover 12 encompasses the filler material 14 and is sealed to a portion of the structure 16. In this regard, the valve structure 16 is fluidly connected to an interior of the cover 12. Notably, the prosthesis 10 is shown FIGS. 1A and 1B in an inflated stated.

In one preferred embodiment, the cover 12 is formed of an outer woven layer of porous, yet high strength material, such as "Dacron"® or "Gortex"®, and an inner layer of a microporous material, such as "Opsite"®. The outer woven layer provides structural support for the cover 12, whereas the inner layer restricts the through flow of fluids from the environment external the cover 12 to those of low molecular weight. The outer layer of the cover 12 is preferably formed of an immunological neutral material, compatible with the tissue found within an intervertebral disc. The inner layer is formed of a transudative (or ion transport) material, and is extended over an interface of the outer layer. With this configuration, tissue within an intervertebral disc space can grow over and incorporate into the outer layer whereas the layer restricts passage of material into the cover to water and very low molecular weight materials. In an alternative embodiment, the cover 12 is comprised of three layers, including an outer layer, an inner layer and a middle layer. With the three-layer approach, the outer and inner layer are made of a strong, immunologically neutral material as previously described. The middle layer is comprised of a transudative material with small pore size.

The filler material 14 is preferably a hydrogel material, which is flowable in a first state and relatively rigid in a second state. In one preferred embodiment, the hydrogel material is polyvinyl alcohol based configured to transition from a liquid form in a first state to a hardened or cured form in a second state. For example, the hydrogel material 14 may be HYPAN®, available from Hymedix International, Inc. Preferably, the hydrogel material 14 has a consistency and swelling pressure of a normal disc nucleus. Additionally, the hydrogel material 14, in an alternative embodiment, may be reinforced by introducing a mesh structure inside the cover 12 and injecting the hydrogel material 14 in a liquid state into the cover 12 such that the hydrogel material 14 cures around the mesh. The resulting structure would be more able to resist stresses in a way similar to the normal disc nucleus. The mesh would be introduced into the cover 12 prior to implant, and may be a fine polypropylene thread. With this configuration, the mesh would easily deform to facilitate insertion of the cover 12 into the nucleus, after which the mesh would spring out once again to fill the cover 12.

Finally, the valve structure 16 preferably includes a one-way valve 18, an extension body 20 and a screw 22. The one-way valve 18 is integrally formed with the extension body 20, the combination of which forms a longitudinal bore 24 through the valve structure 16. The screw 22 is selectively securable to the extension body 20 so as to close the longitudinal bore 24. The one-way valve 18 is shown in FIGS. 1A and 1B as being a conical nose. With this configuration, the conical nose restricts flow of the filler material 14 from the cover 12 through the valve structure 16. Alternatively, the one-way valve 18 may be a flap valve (shown in greater detail below) to further inhibit back flow of the hydrogel material 14 out from the cover 12.

As shown in FIGS. 1A and 1B, the cover 12 is secured about the one-way valve 18 portion of the valve structure 16. The extension body 20 extends from a periphery of the cover 12. Further, in one preferred embodiment, the cover includes a strengthening member 26 positioned opposite the valve structure 16. The strengthening member 26 is preferably formed at an interior of the cover 12, and may assume an arcuate form.

The intervertebral disc nucleus prosthesis 10 is shown in greater detail in FIGS. 2A and 2B. Notably, the prosthesis 10 is shown in a deflated state, with the filler material 14 (FIGS. 1A and 1B) removed from the cover 12 and the screw 22 (FIGS. 1A and 1B) removed from the extension body 22. Additionally, the prosthesis 10 is shown in FIGS. 2A and 2B as being attached to an introducer rod 28 and an external introducer tube 30.

The extension body 20 of the valve structure 16 includes a proximal portion 32 and a distal portion 34. In this regard, the distal portion 34 is connected to the one-way valve 18. The proximal portion 32 includes an external thread 36 and an internal thread 36. The external thread 36 is sized to threadably engage a threaded portion of the external introducer tube 30. Similarly, the internal thread 38 of the extension body 20 is sized to threadably receive a threaded portion of the introducer rod 28.

Use of the introducer rod 28 and the external introducer tube 30 is described in greater detail below. Generally speaking, however, the external introducer tube 30 is an elongated tube defining an internal passage 40. The internal passage 40 of the external introducer tube 30 has a diameter approximating an outer diameter of the extension body 20. The introducer rod 28 is a relatively stiff member having a diameter less than that of the internal passage 40 of the external introducer tube 30. Thus, the introducer rod 28 is coaxially received from the external introducer tube 30. Further, the introducer rod 28 includes a distal end 42 and an intermediate threaded portion 44. As shown in FIGS. 2A and 2B, the intermediate threaded portion 44 threadably engages the internal threaded 38 of the extension body 20. Finally, the introducer rod 28 has a diameter approximating that of the longitudinal bore 24 of the valve structure 16. Thus, the introducer rod 28 can be rotated relative to the valve structure 16 to extend or retract the distal end 42 relative to the strengthening member 26 of the cover 12.

Another feature of the valve structure 16 is shown in greater detail in FIGS. 3A and 3B. As a point of reference, the prosthesis 10 is shown in FIGS. 3A and 3B in an inflated state. Once again, the prosthesis 10 is attached to the external introducer tube 30. However, the introducer rod 28 (FIGS. 2A and 2B) has been removed. Further, the screw 22 has been secured to the proximal portion 32 of the extension body 20. In this secured position, the screw 22 prevents the filler material 14 otherwise maintained within the cover 12 from escaping through the valve structure 16.

FIGS. 3A and 3B also provide an alternative embodiment of the one-way valve 18. More particularly, in the embodiment shown in FIG. 3A, the one-way valve 18 comprises a flap attached at one end to the distal portion 34 of the extension body 20. The flap 18 extends from the extension body 20 within the cover 12 and is able to move within the cover 12. With this configuration, the flap 18 can move to a position by which the flap 18 effectively closes the longitudinal bore 24 in the extension body 20. In this position, the flap 18, in conjunction with the screw 22, prevents back flow of the filler material 14 through the valve structure 16.

A preferred method of implanting the intervertebral disc nucleus prosthesis 10 is substantially as follows. A patient is first extensively imaged by traditional means to obtain the level and condition of a damaged disc 50, in the present case a damaged lumbar disc, as shown in FIGS. 4A and 4B. The disc 50 is basically comprised of an annulus 52 and opposing end plates 54 surrounding a nucleus 56.

Following imaging, the nucleus 56 may be removed as is shown in FIGS. 4A ands 4B. A preferred lateral percutaneous approach to the disc 50 is used whereby an operating port 58 is imparted to access the nucleus 56. A needle (not shown) of appropriate bore is used to enter the nucleus 56 via the operating port 58 and chymopapain is injected to digest the proteoglycan of the nucleus 56. This may be done either prior to the creation of the operating port 58 or through it. A polypropylene bristle brush (not shown) may then be inserted to help break down any remaining structure of the nucleus 56 and to aid the digestion of the nucleus 56, which may be removed by suction.

If necessary a trochar 59 is then passed through the operating port 58 to the posterolateral portion of the annuls 52 and used to expand the operating port 58 by spreading the strong collagenous fibrous tissue of the annulus 52.

Subsequently, the external introducer tube 30, otherwise attached to the prosthesis 10 as previously described, are utilized. More particularly, as previously described with reference to FIGS. 2A and 2B, the distal end 42 of the external introducer tube 30 is secured to the extension body 20 of the valve structure 16. It should be recalled that at this stage, the cover 12 is deflated or empty. In this secured position, the longitudinal bore 24 of the valve structure 16 is aligned with the internal passage 40 of the external introducer tube 30. The introducer rod 28 is then coaxially placed through the internal passage 40 and the longitudinal bore 24 such that the intermediate threaded portion 44 engages the internal thread 38 of the extension body 20. At this point, the introducer rod 28 is rotated such that the opposing threads of the introducer rod 28 and the extension body 20 threadably engage one another. Further rotation of the introducer rod 28 directs the distal end 42 into contact with the strengthening member 26 of the cover 12. Thus, the introducer rod 28 can be extended within the cover 12 to define a preferred diameter of the cover, approximately that of the disc 50 (FIG. 4A).

In one preferred embodiment, a separate tubular screw driver 60 may also be provided, as shown in FIG. 5A. The tubular screw driver 60 includes teeth 62 sized to engage a reciprocal groove 64 in the extension body 20 of the valve structure 16. The teeth 62 are positioned at a distal end 66 of the tubular screw driver 60. Thus, the distal end 66 of the tubular screw driver 60 engages both the external introducer tube 30 and the valve structure 16 to prevent the external introducer tube 30 from disengaging from the valve structure 16. In this regard, it is important to ensure that the valve structure into which the prosthetic cover 12 is attached does not come adrift from the external introducer tube 30 during the insertion process. Finally, the tubular screw driver 60 is secured at a proximal end 68 to the eternal introducer tube 30 as shown in FIG. 5B. More particularly, in one preferred embodiment, the proximal end 68 of the tubular screw driver 60 includes a shoulder 70 sized to fit within a notch 72 in the external introducer tube 30. In other words, placement of the shoulder 70 within the notch 72 prevents the tubular screw driver 60 from rotating relative to the external introducer tube 30.

The surgeon then directs the external introducer tube 30 to insert the cover 12 within the disc 50 as shown in FIGS. 6A and 6B. More particularly, the cover 12 is directed through the operating port S8 in the annulus 52 to the area once occupied by the nucleus 56. The introducer 28 acts as a stiffener, allowing the surgeon to push or force the cover 12 through the annulus 52 and into the area occupied by the nucleus 56. To prevent the introducer rod 28 from piercing the cover 12 during this insertion process, the distal end 42 of the introducer rod 28 is effectively seated against the strengthening member 26.

Notably, the external introducer tube 30 is shown in FIGS. 6A and 6B as a cannula having two proximal ports 74 and 76. Both of the proximal ports 74, 76 are in fluid communication with the internal passage 40. With this configuration, the introducer rod 28 is positioned to extend outwardly from the first proximal port 74. For ease of illustration, the tubular screw driver 60 previously described is not shown.

Once the cover 12 has been properly positioned within the space previously occupied by the nucleus 56, the introducer rod 28 is retracted from the external introducer tube 30. More particularly, the introducer rod 28 is rotated counter clockwise so as to be withdrawn both from the longitudinal bore 24 of the value structure 16 and towards the first proximal port 74. The introducer rod 28 may be fully withdrawn from the first proximal port 74 so long as a cap (not shown) is used to prevent any back flow of the hydrogel material 14.

The filler or hydrogel material 14 is then injected into the cover 12, as shown in FIGS. 7A and 7B which depict the prosthetic cover 12 in a fully inflated state. This is achieved in two possible ways. First, a measured amount of the hydrogel material 14 introduced into a specially designed syringe (not shown) which is introduced into the external introducer tube 30 and locked to the valve structure 16. The hydrogel material 14 is injected into the prosthesis cover 12 so that a piston of the syringe is adjacent the valve structure 16. In a preferred embodiment, the piston of the syringe includes the screw 22 (FIG. 3A) which can be secured to the proximal portion 32 (FIG. 2A) of the extension body 20. A separate screw driver is either incorporated into the piston structure, or inserted down the centre of the piston to engage with the screw 22 which is then turned to engage fully and tighten to the valve structure 16.

Alternatively, the hydrogel material 14 is introduced via the second proximal port 76 and flows down the internal passage 40 of the external introducer tube 30 through the bore 24 in the valve structure 16 and into the deflated prosthetic cover 12 so as to inflate the same to the position shown in FIG. 6A. The introduction of the hydrogel material 14 is continued until the prosthetic cover 12 is adequately filled with the hydrogel material 14.

With reference now to FIG. 8, FIGS. 8A and 8B show sealing of the valve structure 16. The previously described tubular screw driver 60 (FIGS. 5A and 5B) is removed and replaced by a second screw driver (not shown). The second screw driver includes the set screw 22, and is introduced through the external introducer tube 30 and pressed through any remaining the hydrogel material 14 until the screw thread on the sealing set screw 22 comes into contact with the internal thread 38 in the extension body 20 of the valve structure 16. The screw 22 is then rotated to close the bore 24. With the screw 22 secured to the valve structure 16, the eternal introducer tube 30 is then rotated so that it disengages from the prosthesis valve structure 16.

Thus, the tubular screw driver which has a nob to engage the notch in the distal end of the tubular kit introducer is removed and replaced with a second tubular screw driver without a notch so that it can freely rotate with the tubular introducer. It engages with grooves in the valve so preventing rotation of the valve by retaining the tubular screw driver against rotation. The tubular introducer is then rotated so that it disengages for the valve structure whereupon the second screwdriver is removed followed by the operating port.

By means of the foregoing process, a replacement nuclei pulposis can be inserted between adjacent vertebrae successfully with the removal of pain and incapacity, and prevention of the development of secondary degenerative changes in the disc due to the replacement of damaged or degenerated intervertebral disc.

The invention relates therefore to the improved prosthetic device, and to a method for its insertion.

In an alternative form of the prosthesis 10, the valve structure 16 may allow passage of the introducer rod 28 through the flap valve 18 to engage the strengthening member 26. In this latter case, the introducer rod 28 consists of a cannula with an internal trochar having a rounded internal end which engages the strengthening member 26. The prosthesis 10 is inserted by pushing it into the nuclear cavity whereupon the conically nosed trochar is removed. A syringe, containing the hydrogel material 14 is then attached to the external end of the cannula and the hydrogel material 14 injected. Since the internal pressure is greater than the injection pressure, the flap valve 18 will close on removal of the cannula. The hole (or operating port) 58 in the annulus 52 will tend to close as the fibres are stretched, so that the prosthesis 10 which by this time is far greater in size than the operating port 58 is easily retained in position.

What is claimed:

1. In a valve structure adapted for use with a prosthetic device, said structure comprising a body with a longitudinal bore therethrough, said body comprising means for the attachment of a prosthetic cover shaped to form a replacement nucleus pulposis for an intervertebral disc nucleus to the exterior of the structure and means for the reversible attachment of the valve body to an introducer, said introducer allowing injection of a hydrogel material, the improvement which provides that said introducer is adapted to accommodate an introducer rod and that the valve body is adapted to anchor the prosthetic device within a disc space.

2. A valve structure according to claim 1, further comprising obturating means operatively associated with said bore.

3. A valve structure according to claim 2, wherein the bore of the valve body is internally screw-threaded for interengagement with either of the obturating means or introducer rod.

4. A valve structure according to claim 1, wherein said body is generally symmetrical and said bore extends axially of said body.

5. A valve structure according to claim 1, wherein the introducer is engageable generally axially of the valve body by means of a readily reversible interlock.

6. A valve structure according to claim 1, wherein the introducer rod is screw threaded to engage the screw threaded longitudinal bore of the valve structure.

7. A valve structure according to claim 1, formed of an imaging transparent material.

8. A valve structure according to claim 1, wherein a strengthening member is incorporated into the cover and adapted to receive an end of the introducer rod.

9. A valve structure according to claim 1, further comprising a tubular screw driver and wherein the body is provided with engagement means to interlock with the tubular screwdriver, thereby in use to secure the obturating means without dislodgement of the in situ body.

10. A prosthetic cover shaped to form a replacement nucleus pulposis for an intervertebral disc, said cover comprising a permeable layer of an immunologically neutral material terminating in a valve structure to allow the introduction of a hydrogel material, characterized in that a transudative material is disposed on the intended inner faced of the cover to allow a through flow of low molecular weight materials having a molecular cut off below 12,000 daltons.

11. A prosthetic cover according to claim 10, wherein the cover terminates in a one-way valve structure to allow the introduction of the hydrogel material in a normally irreversible manner.

12. A prosthetic cover according to claim 10 wherein the low molecular weight material includes water.

13. A prosthetic cover according to claim 10, wherein the transudative material is formed in a layer which has a size below 9000 daltons.

14. A prosthetic cover according to claim 10, wherein the valve structure comprises an internal conical flap valve to permit the passage of an introducer.

15. A prosthetic cover according to claim 10, wherein a nose section is disposed on the cover in opposed relation to the valve structure and adapted to engage the distal end of the introducer rod during insertion.

16. A prosthetic cover according to claim 10, comprising a valve structure formed of an imaging transparent material.

* * * * *